United States Patent [19]
Sellinger

[11] Patent Number: 5,827,211
[45] Date of Patent: Oct. 27, 1998

[54] ANKLE-FOOT-HEEL PROTECTIVE ORTHOTIC BOOT

[76] Inventor: Daniel J. Sellinger, 708 Leona Dr., Ann Arbor, Mich. 48103

[21] Appl. No.: 769,300

[22] Filed: Dec. 18, 1996

[51] Int. Cl.$^6$ ........................................................ A61F 5/00
[52] U.S. Cl. ................................. 602/27; 602/10; 602/11
[58] Field of Search ................................. 602/5, 6, 9–11, 602/14, 20, 23, 27, 65, 30; 128/869, 878, 881, 882, 889, 892; 36/88–90, 110

[56] References Cited

U.S. PATENT DOCUMENTS

Re. 30,444  12/1980  Spann .
3,511,233   5/1970   Holy, Jr. .
4,076,022   2/1978   Walker .
4,186,738   2/1980   Schleicher et al. .
5,226,245   7/1993   Lamont .

*Primary Examiner*—Linda C. Dvorak
*Attorney, Agent, or Firm*—James M. Deimen

[57] ABSTRACT

An orthotic boot device fittable about an appendage such as a foot to allow support and protection to the skin and underlying tissues covering bony protuberances of the appendage. The device surrounds the appendage and has tapered apertures into which the bony protuberances extend. The tapered apertures fit about the bony protuberances. The thickness of the device body exceeds the extent of the protuberances thereby reducing the likelihood of abrasion or ulceration to the skin covering the bony protuberances.

13 Claims, 2 Drawing Sheets

5,827,211

ANKLE-FOOT-HEEL PROTECTIVE ORTHOTIC BOOT

BACKGROUND OF THE INVENTION

The field of the invention pertains to orthotic devices. In particular, the invention pertains to an orthotic device to prevent and treat ulcerations covering the ankle, foot, heel and toes.

It is known to protect an appendage of a bedridden, neuropathic, physically disabled or otherwise compromised patient with a support to limit the contact and friction of the appendage with traumatic forces.

U.S. Pat. No. Re. 30,444 and U.S. Pat. No. 4,186,738 disclose foam boots with a plurality of ventilation holes. Although certain holes apparently suspend the heel from contact, no provision is made for relief at the ankle sides or either side of the foot adjacent the first and fifth metatarsal bones.

U.S. Pat. No. 3,511,233 discusses a hard outer shell boot with a foam interior. A single hole is provided on the back of the boot adjacent the back of the heel.

U.S. Pat. No. 4,076,022 discloses a device having a plurality of ventilation holes at the bottom and back of the heel.

U.S. Pat. No. 5,226,245 discloses a boot lacking ventilation holes but having an interior fluid filled cushion and an anti-slip sole for ambulatory patients.

The above described orthotic boots are generally intended to only ventilate the foot or at the most support only the heel of the foot from contact. During patient convalescence, certain problems arise, in particular, rubbing of the ankle bones, heel and sides of the foot adjacent to the first and fifth metatarsal bones and toes against a support or boot interior causes abrasion of the skin and eventually ulceration. Mere contact for extended periods of time without movement can cause ulceration leading to infection, osteomyelitis, gangrene and possible loss of limb. The orthotic boot described below seeks to remedy these problems.

SUMMARY OF THE INVENTION

The invention comprises an orthotic boot with relief apertures in specific locations but is not necessarily limited thereto because the principles of the invention are applicable to other appendages. After surgery or during a period of bed rest convalescence, a patient may be immobilized for an extended period of time. Bedridden, disabled and neuropathic individuals may experience ulcerative conditions on the skin and underlying tissues and bone of the ankles, feet, heels and toes. It is common that pressure, decubitus, traumatic, neurotrophic and other ulcerations may occur during an extended period of immobilization.

The new orthotic boot uses a semi-rigid foam material to encase the foot while providing support to the foot and protection to the skin covering the bony protuberances of the ankle, foot, heel and toes. At the bony protuberances the boots are individually relieved by apertures. The skin is thereby protected from frictional engagement and contact with the inside of the boot or with the adjacent bedding. The specific hole patterns and shapes protect the skin over the ankle bones on either side of the foot and the sides of the foot adjacent the first and fifth metatarsal bones and toes. In addition, the outside bottom surface of the boot is fitted for weight bearing and includes a non-slip surface for ambulatory patients.

DESCRIPTION OF THE PREFERRED EMBODIMENT

Figure 1:
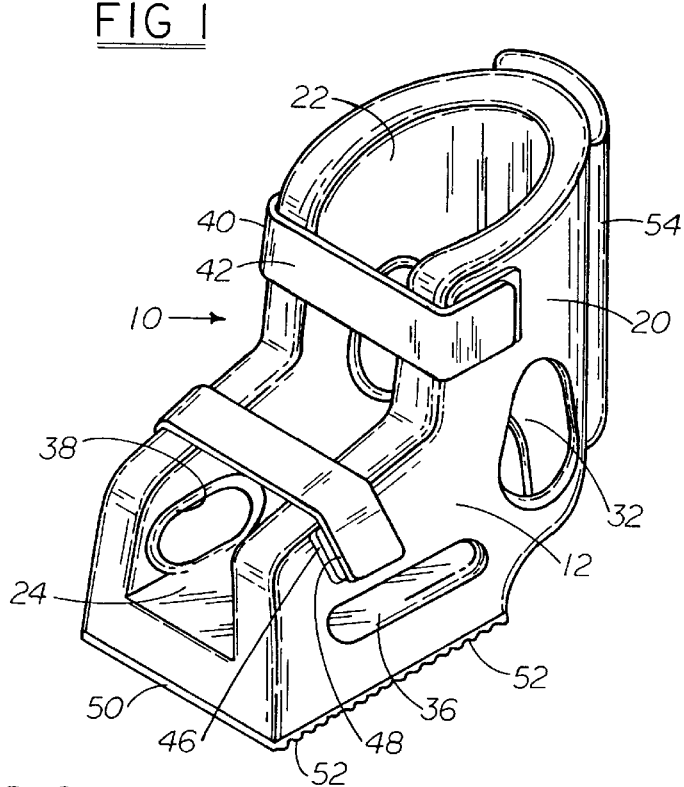
FIG. 1 illustrates a perspective view of the orthotic boot according to the invention.

In FIG. 1, an orthotic boot generally denoted as 10 is shown in perspective view as used. The orthotic boot 10 comprises a body 12 having a boot shape. The body 12 fits a lower leg 14 as shown in phantom in FIG. 2. The lower leg 14 in this instance also includes an ankle 16 and a foot 18. A similar orthotic device could be constructed to protect the knee, elbow or hand area.

The body 12 is formed from semi-rigid foam 20 or other comfortable yet supportive material. A suitable material is a dense polyurethane foam with or without a vinyl outer covering. The material is of sufficient durability, density and thickness to allow for pressure to be relieved from all osseous prominences or cartilaginous protuberances of the foot and ankle in ambulatory, non-ambulatory and insensitive feet. Into the body 12 are formed a first opening 22 and an intersecting second opening 24. A heel aperture 26 is created near the intersection 28 of the first opening 22 and the second opening 24. The body 12 surrounding the first opening 22 generally supports and protects the lower leg including the ankle 16 of the wearer, while the body surrounding the second opening 24 generally supports and protects the foot 18 of the wearer.

An inner ankle aperture 30 (medial malleolus opening) and an outer ankle aperture 32 (lateral malleolus opening) are disposed on opposite sides of the body 12. The ankle apertures 30, 32 extend from outside of the body 12 to connect with the first opening 22. Because the inner ankle prominence of the ankle bone is higher on the leg than the outer ankle prominence, the ankle apertures 30, 32 are slightly different in shape and location to account for this axially tipped positioning of the ankle bone relative to the leg and foot.

An aperture 34 for the large toe joint at the ball of the foot (first metatarsal head opening) is disposed on the same side of the body 12 as the inner ankle aperture 30. Along the opposite side from the large toe joint aperture 34 an elongated aperture 36 (fifth metatarsal head and styloid process opening) is formed to accommodate the outer side of the foot adjacent the small toe joint and ball. The elongated aperture 36 is disposed on the side where the outer ankle 32 is located. The placement and relationship of the apertures can be seen in FIGS. 1–3.

The apertures 30, 32, 34 and 36 all are chamfered, skived or tapered inwardly 38 causing the aperture walls to enlarge towards the openings 22 and 24 in the body 12 relative to where the apertures intersect the outside of the body. This tapering allows the bony protuberances of the foot to readily fit into the apertures. The tapering of the apertures lessens the likelihood of abrasion or ulceration of the skin adjacent the bony protuberances. The thickness of the body 12 allows the full extension of the bony protuberances to remain below or inside the body. Consequently, by maintaining the bony protuberances inside the body with adequate properly located apertures, the potential for abrasion or ulceration is dramatically reduced.

The orthotic boot 10 is to be custom fitted (by cutting and skiving the foam) through girth and bony landmark measurements of the ankle, foot and heel. Although the orthotic boot 10 is shown as placed on one foot and ankle, the placement of the apertures can be reversed in mirror image for the other foot.

Further, means 40 are employed to retain the boot 10 on the foot 18. The means 40 for retaining the foot can be straps 42 as hereshown or elastic bands. In conjunction with the straps 42 or elastic bands, fastening means 44 are employed at each end of the straps 42 or bands to join to the body 12. Hook 46 and loop 48 fasteners are advantageously deployable for this purpose. Other fasteners such as snaps or tied fasteners are also feasible.

The body 12 includes a reinforced outer sole 50 designed to bear weight as needed for ambulatory patients. A slip resistant tread 52 is formed on the sole 50 of the body 12 to reduce the possibility of slipping when walking for those patients who are ambulatory.

Figure 2:
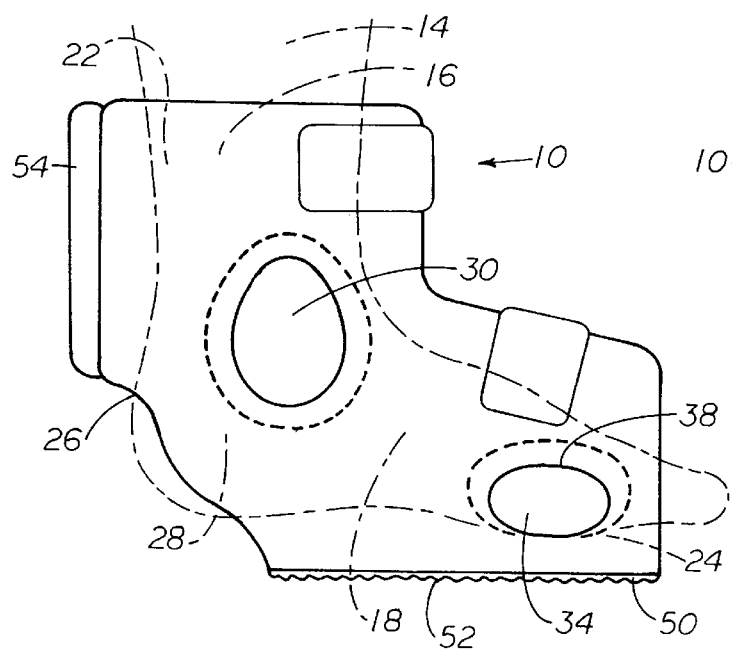
FIG. 2 illustrates a side view of the other side of the orthotic boot.
Figure 3:
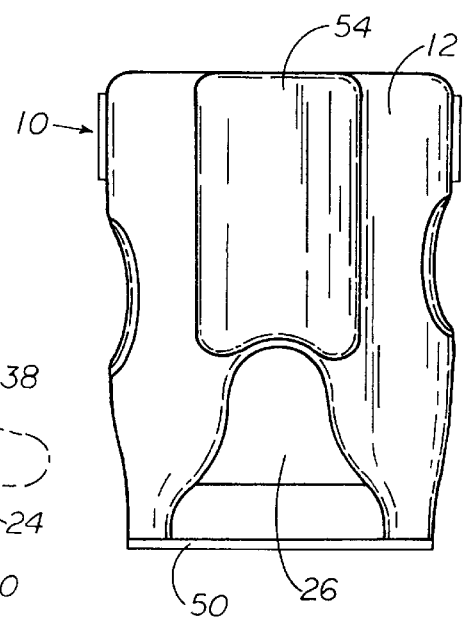
FIG. 3 illustrates a back view of the orthotic boot.

In use, the foot of the patient is inserted into the openings 22 and 24 in the body 12 of the device. The bony protuberances of the foot and ankle are positioned to fit into the apertures. Then the straps 42 of the device are placed over the instep and attached to the body of the device as shown in FIGS. 1 and 2.

In most use, the patient is bedridden and the device 10 rests "toes up" with the weight of the foot 18 and lower leg 14 generally about the lower leg surrounding the achilles tendon area. Therefore, added cushioning may be provided as shown at 54 to distribute the weight more evenly.

Figure 4:
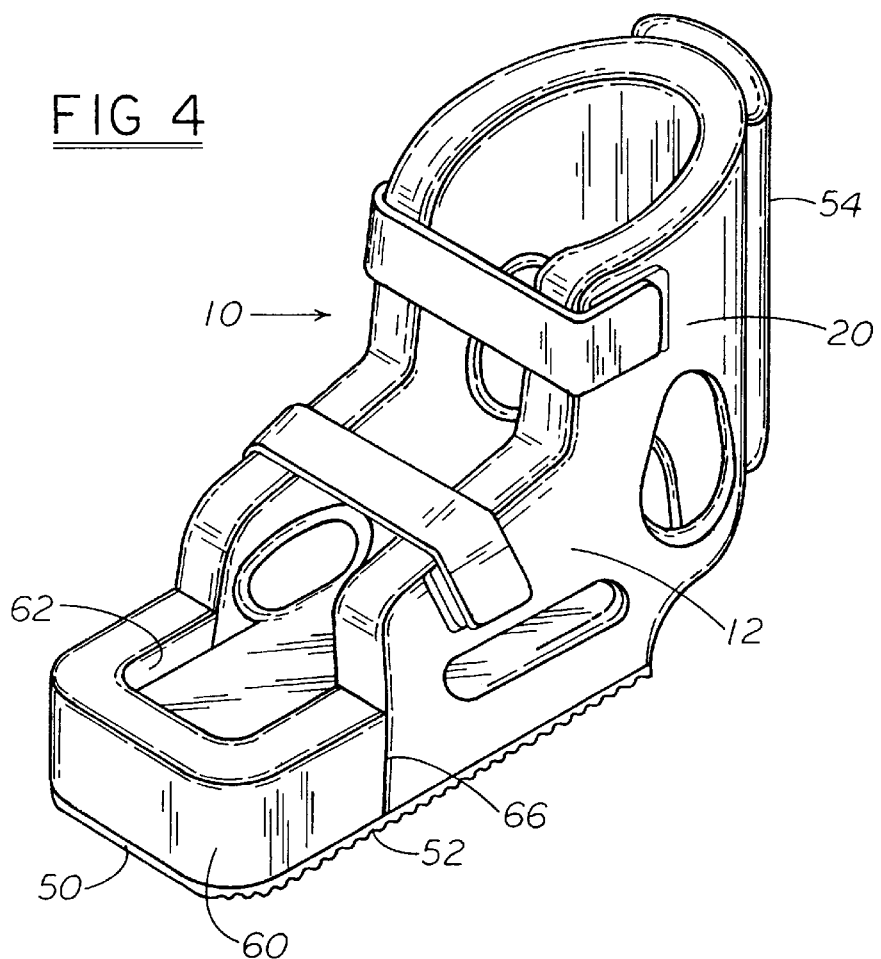
FIG. 4 illustrates a perspective view of an alternate form of the orthotic boot.
Figure 5:
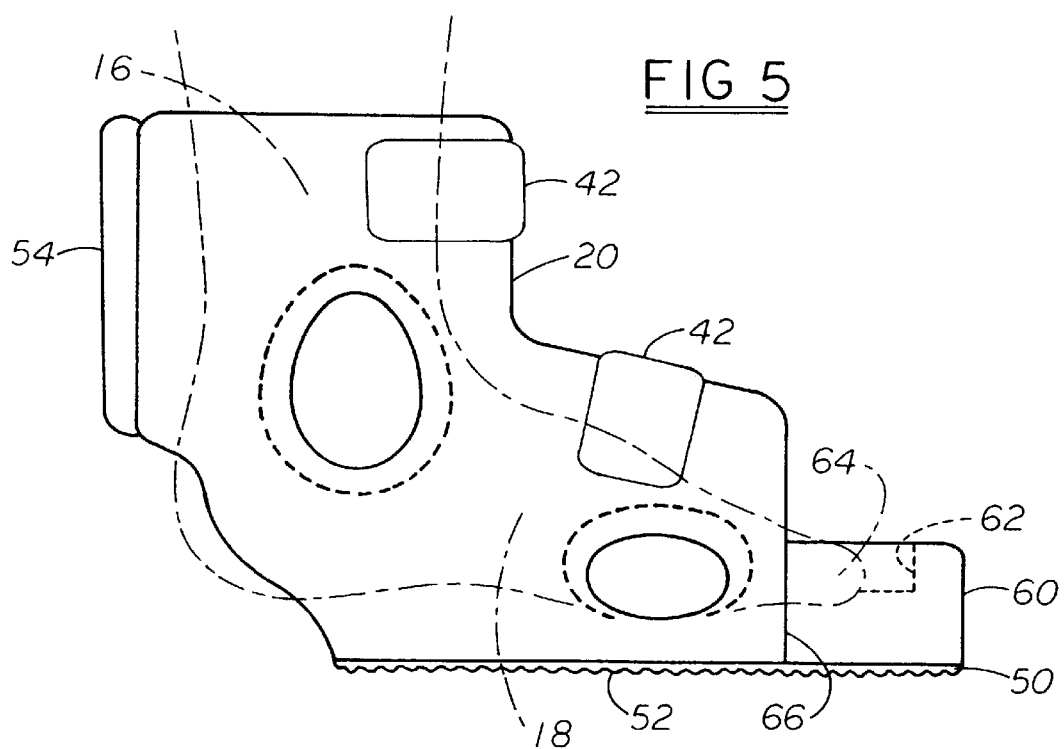
FIG. 5 illustrates a side view of the orthotic boot of FIG. 4.

FIGS. 4 and 5 illustrate a modified orthotic boot 10 that includes a toe protector extension 60 having a cavity 62 into which the toes 64 project. The toe protector 60 may be adhesively or mechanically attached to the body 12 at 66 or be formed integral with the body 12. The outer sole 50 and tread 52 extend fully beneath the body 12 and toe protector 60. With the toe protector 60 bed sheets and other coverings are kept well above the toes 64. For the ambulatory patient, the toes 64 are better protected from inadvertent injury.

I claim:

1. An orthotic device fittable about an appendage having bony protuberances, the device comprising a body having an outside and a first opening thereinto, the body having a second opening thereinto, and the body having a third opening thereinto, the first opening intersecting the second opening to fit about the appendage placed in the openings, the third opening intersecting the intersection of the first opening and the second opening, and the third opening being formed to surround a heel of a foot on the appendage, and the body having at least one aperture disposed between the outside of the body and one of the first and second openings, the aperture located on the body to surround a bony protuberance of the appendage, and the aperture having walls, the walls of the aperture being tapered between the opening and the outside of the body.

2. The orthotic device according to claim 1 wherein the aperture is formed to surround a bony protuberance on an ankle of the appendage.

3. The orthotic device according to claim 2 wherein a second aperture is formed to surround a bony protuberance on a second portion of an ankle of the appendage.

4. The orthotic device according to claim 1 wherein the aperture is formed to surround a bony protuberance at the large toe joint of a foot of the appendage.

5. The orthotic device according to claim 1 wherein the aperture is formed to surround a bony protuberance at the lateral side of a foot of the appendage, the side of the foot being opposite a side having a large toe joint.

6. An orthotic device fittable about an appendage having bony protuberances, the device comprising a body having an outside and a first opening thereinto, the body having a second opening thereinto, and the body having a third opening thereinto, the first opening intersecting the second opening to fit about the appendage placed in the openings, and the third opening intersecting the intersection of the first opening and second opening, and the body having at least one aperture disposed between the outside of the body and one of the first and second openings, the aperture located on the body to surround a bony protuberance of the appendage, and the aperture having walls that enlargingly taper from the outside of the body to the opening within the body.

7. The orthotic device according to claim 1 wherein the device comprises a dense supportive foam.

8. The orthotic device according to claim 1 wherein the device comprises a soft dense supportive foam capable of being formed to fit by custom forming the aperture and skiving the aperture walls.

9. The orthotic device according to claim 1 wherein the device has a sole, the sole including a non-slip tread.

10. The orthotic device according to claim 1 wherein the device further comprises means for retaining the device on an appendage.

11. The orthotic device according to claim 10 wherein the means for retaining the device on the appendage comprises strapping with hook and loop fasteners.

12. The orthotic device according to claim 1 including a toe protector comprising an extension of the body beyond the second opening and a cavity in the toe protector forming an extension of the second opening.

13. A method of preventing abrasions and ulceration of an appendage comprising forming a generally hollow shaped body having openings adapted to fit over a portion of the appendage, measuring the locations of bony protuberances on the appendage and forming apertures in the body generally coinciding with the bony protuberances, skiving the apertures to enlargingly taper the walls of the apertures toward the openings in the body, placing the appendage in the body and, attaching retention means to the body to retain the appendage in the body.

* * * * *